United States Patent [19]

Kussmaul et al.

[11] Patent Number: 4,677,209
[45] Date of Patent: Jun. 30, 1987

[54] PROCESS FOR THE PREPARATION OF 2-MERCAPTOBENZOXAZOLES

[75] Inventors: Ulrich Kussmaul, Karben; Manfred Langer; Kuno Reh, both of Frankfurt; Johannes Becherer, Maintal; Herbert Wille, Frankfurt; Rolf Müller, Karben, all of Fed. Rep. of Germany

[73] Assignee: Cassella Aktiengesellschaft, Frankfurt am Main, Fed. Rep. of Germany

[21] Appl. No.: 844,603

[22] Filed: Mar. 27, 1986

[30] Foreign Application Priority Data

Apr. 4, 1985 [DE] Fed. Rep. of Germany ....... 3512295

[51] Int. Cl.$^4$ ........................................... C07D 263/58
[52] U.S. Cl. .................................... 548/221; 548/101
[58] Field of Search ................................. 548/101, 221

[56] References Cited

U.S. PATENT DOCUMENTS 4,442,294  4/1984  Handte et al. ...................... 548/221

OTHER PUBLICATIONS

Handte et al, CA 98-107280s.
Dünner, Chem. Ber. 9 (1876) 465–466.
Chemical Abstracts, vol. 49, Nr. 17, Sep. 10, 1955, Columbus, Ohio, *Benzoxazole Derivatives, i. 2-Mercaptobenzoxazoles,* by Leon Katz and Murray S. Cohen, p. 11623.
Chemical Abstracts, vol. 45, Nr. 1, Jan. 10, 1951; Columbus, Ohio; *2-Mercaptobenzimidazole,* by J. A. VanAllan and B. D. Deacon; p. 158.
Chemical Abstracts, vol. 99, Nr. 23, Dec. 5, 1983, Columbus, Ohio; *Synthesis of 3-Substituted Benzoxazoline-2-Thiones,* by Yamato, Masatoshi; Takeuchi, Yasuo; Hashigaki, Kuniko et al.
Chemical Abstracts, vol. 78, Nr. 15, Apr. 16, 1973, Columbus, Ohio: *Cleavage of 3-Benzoylbenzoxazolinones and their Monothioxoisologs with Hydroxide and Methoxide,* by Wagner, G.; Leistner, S.
Chemical Abstracts, vol. 93, Nr. 25, Dec. 22, 1980, Columbus, Ohio; *A Direct Synthesis of Heterocyclic Thiols,* by William O. Foye; Norman Abood, Joel M. Kauffman, Patel Young-Ho et al.

*Primary Examiner*—Nicholas S. Rizzo
*Assistant Examiner*—Cecilia Shen
*Attorney, Agent, or Firm*—Connolly and Hutz

[57] ABSTRACT

2-Mercaptobenzoxazoles of the formula

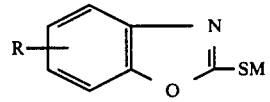

wherein R is hydrogen or halogen and M is hydrogen or a metal atom, are prepared by reacting an orthoaminophenol or metal salts thereof, with an alkali metal trithiocarbonate in aqueous solution.

6 Claims, No Drawings

PROCESS FOR THE PREPARATION OF 2-MERCAPTOBENZOXAZOLES

The present invention relates to a process for the preparation of 2-mercaptobenzoxazoles of the formula I

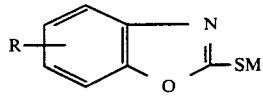

wherein R denotes hydrogen or halogen and M denotes hydrogen or a metal atom. The compounds of the formula I are useful precursors for the preparation of highly active herbicides. There is therefore an urgent need for an inexpensive and at the same time low-polluting process for the preparation of these compounds.

2-Mercaptobenzoxazole has already been described in 1876 by Dünner (Ber. 9, (1876) page 465). 2-Mercaptobenzoxazole and its derivatives are prepared by processes which are based in principle on the reaction between o-aminophenol and alkali metal alkylxanthates. The alkali metal alkylxanthate here can either be employed as such, or it can be produced in the reaction mixture itself from an alkali, a lower alkanol and carbon disulphide.

The known processes have, however, considerable disadvantages which make it considerably more difficult to convert them to the large industrial scale. Thus, carbon disulphide can be used only in special explosion-proof apparatuses, a residual risk which is difficult to calculate always remaining. The use of relatively large amounts of alkanols is also unfavourable, since they must be recyclised as quantitatively as possible and losses lead to pollution of the effluent, associated with increased effluent purification costs.

A process by which compounds of the formula I can be prepared in good yields is known from European Patent Application No. 66,248. However, this process also additionally has disadvantages, some of which manifest themselves only in the large-scale industrial procedure and make this considerably more difficult. Thus, in this case also, an alkali metal alkylxanthate is reacted with aminophenols, it being possible for the reaction to be carried out in an organic solvent or also in water. Metering of the solid alkali metal alkylxanthates, which are available on a large industrial scale, which is necessary here requires particular technical effort and particular environmental protection measures because of the formation of dusts.

Carry out the process according to the prior art in an organic solvent requires an increased expenditure for regeneration of these solvents and for removal of alcohols. If the process is carried out in water, an effluent polluted with alcohols (from the xanthates) is obtained and must be purified by physical, chemical or biological methods. For example, this alcohol results in an increased CSB/BSB5 pollution and requires additional expenditure in biological treatment of the effluent. Furthermore, the large-scale industrial implenentation of the process according to the prior art has shown that, in addition to hydrogen sulphide, the waste air contains lower alkylmercaptans which are a substantial odour-nuisance and either are already contained as mercaptides in the xanthates employed or are formed from these.

It has now been found that the disadvantages of the previously known preparation processes can be avoided if, to prepare the compounds of the formula I, an aminophenol of the formula II

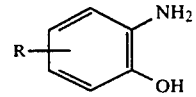

wherein R has the abovementioned meanings, or a metal salt thereof, in particular an alkali metal salt thereof, is reacted with an alkali metal trithiocarbonate in aqueous solution.

The sequence in which the reaction components are combined is insignificant for the process. Thus, a solution or suspension of the aminophenol of the formula II or a metal salt thereof in water can be taken and the alkali metal trithiocarbonate, preferably in the form of an aqueous solution, can be metered in during the reaction. However, the reaction can also be carried out by the reverse operation, if there is an industrial necessity for this. All the reaction components, that is to say the aminophenol or a salt thereof, alkali metal trithiocarbonate and water, can, however, also first be mixed and then kept at the desired reaction temperature. The reaction temperature can be varied within wide limits and depends on the given possibilities of the plant. Thus, although carrying out the reaction at a normal temperature of 20° C. is accompanied by a saving in heating costs and can be undertaken in the simplest of all apparatuses, it unavoidably leads to a drastic lengthening of the reaction time. On the other hand, a very short reaction time can be achieved by working at 150° C. if a corresponding apparatus is available and a certain reduction in the quality of the product is acceptable. The reaction is preferably carried out in the temperature range from 50° to 120° C.

It goes without saying that for the reaction procedure above about 100° C., the reaction is carried out in a closed vessel under the corresponding vapour pressure of the reaction mixture.

As a rule, 1.00 to 1.2, preferably 1.00 to 1.1 or with larger batches in particular 1.02 to 1.06, moles of alkali metal trithiocarbonate are employed per mole of aminophenol of the formula II.

The process according to the invention can be carried out particularly conveniently and economically by using technical grade alkali metal trithiocarbonates, in particular in the form of commercially available aqueous solutions. During the reaction an alkaline pH value establishes itself which, however, is not high enough to prevent the $H_2S$, which has been formed, from escaping.

As the equation of the reaction on which the process according to the invention is based shows, during the formation of the oxazole nucleus, two moles of sulphidic sulphur are released part of which is in equilibrium as $H_2S$ and is released from the reaction mixture. If the occurrence of free $H_2S$ is to be prevented, at least 1 gram equivalent of alkali which binds, in the form of a sulphide, the hydrogen sulphide split off can be added to the reaction mixture per mole of the aminophenol of the formula II. In this case, the reaction is advantageously carried out with a certain excess of alkali. If the reaction is carried out in a closed system under a small excess pressure, for example under 0.02 to 0.2 bar, such as results, for example, when the reaction kettle is closed by a liquid seal, 102 to 110% of the theoretically required amount of alkali are usually employed. If, in practice, the occurrence of free $H_2S$ during the reaction is also to be reliably avoided in an open procedure, it is advantageous to add 2 to 3 gram equivalents of alkali. Suitable alkalis are, above all, alkali metal hydroxides, such as NaOH or KOH, and salts of alkali metals with acids which are weaker than $H_2S$ and are therefore capable of bonding $H_2S$ as a sulphide.

When the reaction has ended, as a rule aqueous solutions, or with very highly concentrated batches aqueous dispersions, of the alkali metal salts of the benzoxazole derivatives of the formula I are obtained, and in many cases can be employed directly for further reactions.

If the aqueous solutions are not to be further processed directly, the resulting 2-mercaptobenzoxazoles of the formula I can also be isolated in a manner which is known per se. For this purpose, it is usual to acidify the resulting aqueous solution or dispersion by addition of, preferably, an inorganic acid to the extent that, according to the $pK_a$ value of the mercaptobenzoxazole prepared, complete precipitation of the product occurs (pH about 0–4), and, if the $H_2S$ formed during the reaction has been trapped by addition of alkali, to absorb the hydrogen sulphide which may be driven off. The mercaptobenzoxazole derivative of the formula I liberated from the alkali metal salt on acidification precipitates and can be isolated by a solid/liquid separation operation, preferably by filtration. The filtrate thereby obtained, in contrast to that obtained after the xanthate process, is an effluent with only low pollution.

The process according to the invention enables the reaction to be carried out conveniently in open or closed vessels, under atmospheric pressure or under pressure, batchwise or continuously. If the reaction mixture is sufficiently alkaline, an absorption plant for hydrogen sulphide during the reaction can thus be completely dispensed with.

The process according to the invention is particularly useful for the preparation of those compounds of the formula I in which R denotes fluorine, chlorine or bromine, but in particular chlorine, or hydrogen. The preparation of those compounds of the formula I in which R is in the 6-position of the benzoxazole system is particularly preferred.

2-Mercaptobenzoxazole is obtained by the process according to the invention if 2-aminophenol is employed as the starting material of the formula II; to prepare a 6-halogeno-2-mercaptobenzoxazole, 5-halogeno-2-aminophenols are correspondingly used as starting substances.

Preferred meanings of M are alkali metal atoms, in particular Na and K, and hydrogen.

Those compounds of the formula I in which several preferred features are combined are particularly preferably prepared.

It is surprising to the expert that the advantageous and low-polluting process according to the invention gives the same good yields with short reaction times as the xanthate process which is difficult to carry out on a large industrial scale, although, according to the Law of Mass Action, it is in theory considerably disadvantageous.

Thus, during the cyclisation reaction by the xanthate process according to European Pat. No. 66,248, vigorous evolution of hydrogen sulphide is observed. reaction product is thus continuously withdrawn from the reaction equilibrium, which, according to the Law of Mass Action, promotes the advance of the reaction.

Surprisingly, in the process according to the invention, the desired products of the formula I are obtained in the same yields and purities at the same reaction time, although, in comparison with the xanthate process, a further mole of sulphidic sulphur is additionally added as trithiocarbonate to the reaction mixtures, which must be evaluated as adverse in the context of the Law of Mass Action. It must be regarded as extremely surprising that the reaction even then still proceeds as rapidly as in the xanthate process if the evolution of hydrogen sulphide and removal thereof from the reaction mixture during the reaction is completely suppressed by addition of sodium hydroxide solution.

The following embodiment examples illustrate the process according to the invention.

EXAMPLE 1

170.8 g of 84.1% strength 5-chloro-2-aminophenol, 336.9 g of 48% strength sodium trithiocarbonate, as an aqueous solution, 121.6 ml of sodium hydroxide solution of 33°Be strength and 250 ml of water are mixed in a stirred flask with a thermometer and reflux condenser, the reaction vessel is sealed with a 1 m high column of brine and the mixture is boiled under reflux for 3 hours, while stirring continuously. The batch is cooled and the resulting 6-chloro-2-mercaptobenzoxazole is precipitated in a known manner by addition of sulphuric acid and filtered off and the filter cake is washed salt-free with water and dried at 80° C. in vacuo.

179 g of 6-chloro-2-mercaptobenzoxazole (corresponding to 96% of theory) of melting point 223°–224° C. are obtained.

If the reaction is carried out at 80° C., a yield of 95% of theory is obtained after a reaction time of 24 hours; at 150° C. in a closed reaction, the cyclisation proceeds in less than 1 hour, and a yield of 90% of theory is thereby obtained.

EXAMPLE 2

170.8 g of 84.1% strength 5-chloro-2-aminophenol are suspended in 350 ml of water in a stirred flask with a thermometer and reflux condenser. The suspension is warmed to 95° to 100° C. and a solution of 336.9 g of a 48% strength by weight aqueous sodium trithiocarbonate solution is metered in at this temperature in the course of 3 hours, while stirring. Thereafter, the mixture is boiled under reflux for a further 3 hours. After working up of the resulting solution as in Example 1, 181 g (97% of theory) of 6-chloro-2-mercaptobenzoxazole of melting point 221° to 223° C. are obtained.

If the 5-chloro-2-aminophenol in one of Examples 1 or 2 is replaced by 109.1 g of pure or 116.1 g of technical grade 94% strength 2-aminophenol, 98% of theory, according to Example 1, or 96% of theory, according to Example 2, of 2-mercaptobenzoxazole of melting point 192° to 193° C. is obtained.

If the reaction is carried out at 50° C., the mixture must be stirred for more than 24 hours in order to obtain a yield of at least 90% of theory.

What we claim is:

1. Process for the preparation of 2-mercaptobenzoxazoles of the formula

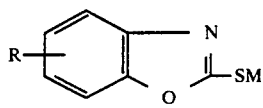

wherein R is hydrogen or halogen and M is hydrogen or an alkali atom, which comprises reacting an alkali metal trithiocarbonate in aqueous solution with an aminophenol of the formula

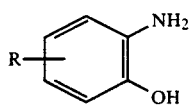

or a metal salt thereof.

2. Process according to claim 1 wherein the reaction is carried out at temperatures from 20° to 150° C.

3. Process according to claim 2 wherein the reaction is carried out at temperatures from 50° to 120° C.

4. Process according to claim 1 wherein the reaction is carried out in the presence of 1 to 3 gram equivalents of an added alkali metal hydroxide.

5. Process according to claim 1 wherein the aminophenol is 2-aminophenol or 5-chloro-2-aminophenol.

6. Process for the preparation of 2-mercaptobenzoxazoles of the formula

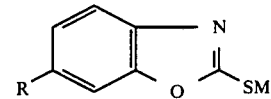

wherein R is hydrogen or chloro and M is hydrogen or a metal atom, which comprises reacting 2-aminophenol or 5-chloro-2aminophenol with an alkali metal trithiocarbonate in aqueous solution at an alkaline pH value at 50° to 120° C.

* * * * *